United States Patent [19]

Mark

[11] 4,321,202
[45] Mar. 23, 1982

[54] 1-METHYL-2(ALKYLIMINO)PYRROLI-DINES AND 1-METHYL 2(CYCLOALKYLIMINO) PYRROLIDINES

[75] Inventor: Victor Mark, Evansville, Ind.

[73] Assignee: General Electric Company, Mt. Vernon, Ind.

[21] Appl. No.: 106,677

[22] Filed: Dec. 26, 1979

[51] Int. Cl.$^3$ .................. C07D 207/22; C07C 123/00
[52] U.S. Cl. ............................. 260/326.86; 564/225; 564/244; 564/245; 260/239 A; 260/944; 260/968; 546/229
[58] Field of Search ................................... 260/326.86

[56] References Cited

PUBLICATIONS

Ellingsfeld et al., Angew. Chem., 72 (1960), pp. 836–845.

*Primary Examiner*—Donald G. Daus
*Assistant Examiner*—D. B. Springer
*Attorney, Agent, or Firm*—Martin B. Barancik; William F. Mufatti

[57] ABSTRACT

Amidines are one of the strongest organic bases and find application where this property is needed, such as in phase transfer catalysis in the form of their substituted derivatives. Their use, however, has been hampered by their expensive nature due to only mediocre yields in their preparation. The present invention provides a process for the preparation of substituted amidines in essentially quantitative yields.

1 Claim, No Drawings

1-METHYL-2(ALKYLIMINO)PYRROLIDINES AND 1-METHYL 2(CYCLOALKYLIMINO) PYRROLIDINES

Amidines are one of the strongest organic bases and find application where this property is needed, such as in phase transfer catalysis in the form of their substituted derivatives. Their use, however, has been hampered by their expensive nature due to only mediocre yields in their preparation. The present invention provides a process for the preparation of substituted amidines in essentially quantitative yields.

BACKGROUND OF THE INVENTION

One of the most general methods for preparing substituted amidines (B), (B'), and (B") is from substituted (methylammonium) (also called substituted formiminium halides), represented by formulae (A), (A') and (A") with primary amines and ammonia

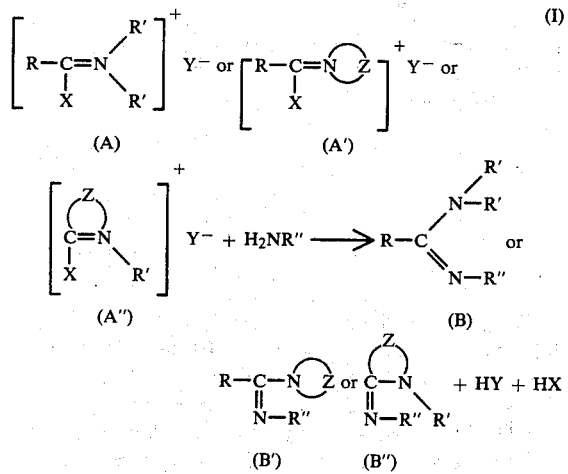

or with secondary amines

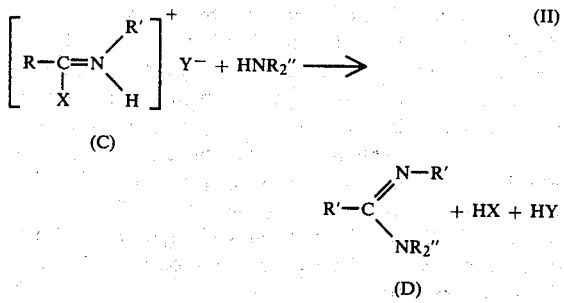

wherein R is a monovalent substituent selected from the group consisting of hydrogen, alkyl, aryl, aralkyl, alkaryl, cycloalkyl, alkenyl, cycloalkenyl and heterocyclic radical; R' and R" are monovalent organic radicals independently selected from the group consisting of alkyl, aryl, aralkyl, alkaryl, cycloalkyl, alkenyl, cycloalkenyl and heterocyclic radical; X is a monovalent substituent selected from the following radicals: —OP(O)Cl$_2$; —OPCl$_4$, —O—S(O)Cl, —O—S(O)—R, and —O—C(O)—R; Y is chlorine or bromine; and Z is a divalent organic radical completing a 4 to 8 membered cycloaliphatic ring and containing (i) from 2 to 6 carbon atoms or (ii) from 2 to 6 carbon atoms and one hetero atom selected from the group consisting of oxygen, sulfur and nitrogen with the proviso that no hetero atom is adjacent the nitrogen atom.

The processes are illustrated (a) in the book by P. A. S. Smith, *Open Chain Nitrogen Compounds*, Vol. 1, pp. 177-184 (1965), W. A. Benjamin, Inc., New York; (b) in the review article by R. L. Schriner and F. W. Neumann, in *Chemical Reviews*, Vol. 35, pp. 351-425 (1944); (c) *Angewandte Chemie*, Vol. 72, pp. 836-845 (1960) and in individual papers, such as (d) *Chemische Berichte*, Vol. 92, pp. 837-849 (1959). The yields, however, are only mediocre, usually between 40 and 70%, and drastic heating conditions (between 150° and 180° C.) are required to effect reactions with the more basic amines (as shown in reference (d), p. 839).

SUMMARY OF THE INVENTION

It has now been found that reactions I and II can be made facile and essentially quantitative by adding together with the primary or secondary amines one of the followind co-reactants:

(a) at least one, but preferably two, moles of a tertiary amine of high basicity;

(b) at least one, but preferably two, moles of a strong inorganic base;

(c) at least one, but preferably two, additional moles of the primary or secondary amine reactant;

(d) at least one, but preferably two, moles of the amidine product formed in the reaction.

The role of the strong base in reaction I is not only to liberate the amine reactant that is partially inactivated by being tied up as its hydrochloride, but to participate actively in the reaction, which is shown in its simplified form by equations I and II. Actually, there are reaction intermediates such as (E) and (F) between the reactants such as (A) and the amidine products produced such as (B):

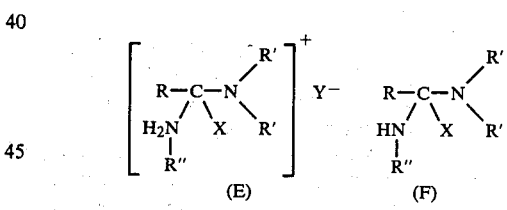

wherein X, Y, R, R' and R" are as above.

The added organic or inorganic base facilitates the conversion of these intermediates such as (E) and (F) to (B), thus not only increasing the yield, but the reaction rate as well. Therefore, the high reaction temperature (150° to 180° C.), necessary for the reaction of the halides with strongly basic amines when used in the stoichiometrically required amounts (ref. (c) above) are no longer needed since the reaction can, in fact, now proceed exothermally in the presence of the added organic or inorganic base.

Examples of the strong inorganic bases that can be employed are alkali or alkaline earth metal hydroxides, such as sodium hydroxide, potassium hydroxide, calcium hydroxide, and the like.

The strong organic bases which can be employed are tertiary aliphatic and cycloaliphatic amines, dialkyl amidines, di- or poly (tertiary) amines, and the like. Examples of such strong organic bases include triethyl amine, tripropyl amine, tributyl amine, dicyclohexylmethyl amine, diiospropylamine, quinuclidine, hexamethylenetetramine, and the like.

In one of the preferred embodiments, the extra organic base is the primary amine itself ($H_2NR''$) of equation I such as methylamine, ethylamine, propylamine, isopropylamine, butylamine, octadecylamine, aniline, p-chloroaniline, 4-amino-pyridine, ethanolamine, 2-methoxyethylamine and similar substituted aliphatic, cycloaliphatic, aromatic and heterocyclic amines. Examples of secondary amines include dimethylamine, diethylamine, diisopropylamine, methylbutylamine, ethylcyclohexylamine, pyrrolidine, piperidine, morpholine, N-methylaniline, diethanolamine, and the like.

In another preferred embodiment, the extra organic base is the amidine itself; that is, the reaction product of equations I and II. This is a particularly preferred variation since amidines are more powerful bases than any of the tertiary amines or the primary amines required in equation I or the secondary amines of equation II and are thus capable to effect quantitative conversions. Furthermore, the reactions are especially clean since there are no extraneous products formed and there is, thus, no need for extra separation steps, such as distillation. The amidine tied up in the reaction as its hydrochloride can be set free at the end of the reaction by concentrated aqueous sodium hydroxide solution and reused anew.

The preparation of the amidine precursors of reactions I and II are best prepared by the reaction of the appropriate carboxylic acid amide with one of the following reactants: $PCl_5$, $P(O)Cl_3$, $SOCl_2$, $RS(O)Cl$, and $R'C(O)Y$ as for example:

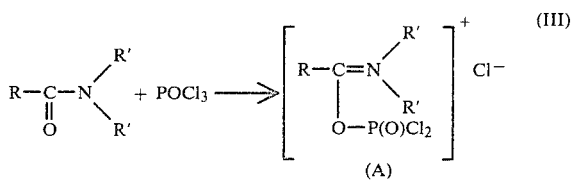

(III)

(A)

wherein R and R' are as above.

Preparative methods for (A) and (C) are given in references (a) at pp. 147-148, 177-184 and 272; (c), and in (d) *Chemische Berichte*, Vol. 92, pp. 837-849 (1959).

The preparation of amidines is best carried out without the isolation of (A), (A'), (A") and (C) which are moisture sensitive. Instead, reactions III and I, and III and II, are best combined and carried out in the same reactor, with complete exclusion of moisture, to secure maximum, often quantitative yields. It is, therefore, best to add the halogen containing reactant to a solution or slurry of the carboxylic acid amide in an inert liquid until the reaction is completed, as evidenced by the abatement of the exothermic reaction, and then introduce the amine reactant in excess or in the presence of the tertiary amine or amidine. The reaction is facile, and usually exothermic. Internal (such as by the refluxing solvent) or external cooling is applied to maintain the reaction temperature at optimum levels, which is between 0° and 100° C., preferably 30° and 50° C. When inorganic bases are used, they are best introduced after the theoretical amount of primary amine has been added. Preferably, the addition of the inorganic base is gradual, so as to minimize the hydrolysis of (A), (A'), (A") and (C) back to the amides. It is alos best to use relatively concentrated (30–50%) solutions of sodium or potassium hydroxide or slurries of calcium hydroxide or barium hydroxide. If the amidine formed is a liquid, it is best separated from the aqueous brine by phase separation and purified distillation. If solid, it is best filtered off, washed, dried and eventually recrystallized.

DETAILED DESCRIPTION OF THE INVENTION

The invention will become more clear when considered together with the following examples, which set forth the best mode presently known for practicing the inventive process.

EXAMPLE 1

N,N-Dimethyl-N'-phenylbenzamidine

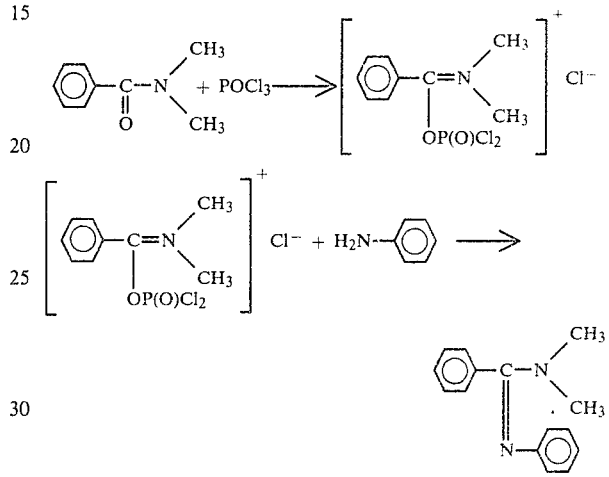

This example illustrates the preparation of N'-phenyl-N,N-dimethylbenzamidine (PDMB) by conventional methods known in the prior art such as shown in references (a), (b), (c) and specifically in (d) given above.

To a mixture obtained by adding a solution of 23.1 g of phosphorus oxychloride in 50 ml of benzene to 37.2 g of N,N-dimethylbenzamide in 50 ml of benzene, there was added a solution of 14 g of aniline in 40 ml of benzene. The strongly exothermic reaction during the $POCl_3$ addition was moderated by external cooling. After completion of the aniline addition at 35°–40° C., the reaction mixture was kept at 65°–70° C. for 6 hours. Water and dilute hydroxide treatment yielded a solution, which, after the stripping of the solvent yielded N,N-dimethyl-N'-phenylbenzamidine, b.p. 122°–124° C. at 0.15 mm of mercury pressure, which solidified. Recrystallized from hexane, the amidine had a melting point of 70°–71° C. The yield was 17.4 g (0.078 mole) or 52% of the theory based on aniline or only 31.2% based on the benzamide.

EXAMPLE 2

This example illustrates the preparation of the amidine of Example 1 by the improved process of the invention.

The procedure of Example 1 was repeated except that after the addition of 38.3 g of $POCl_3$ in 250 ml of benzene, a solution of 23.3 g of aniline in 100 ml of triethylamine was added, with efficient cooling. Workup by water and caustic treatment and distillation yielded 50.6 g (0.226 mole) of the amidine, thus raising the yield to 90.3% based on both the benzamide and aniline.

EXAMPLE 3

N,N-Dimethyl-N'-phenylacetamidine

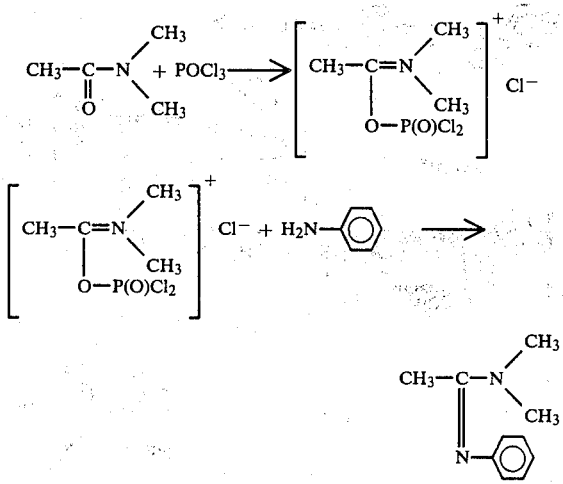

The conventional procedure of Example 1 was repeated except that 32.7 g (0.375 mole) of N,N-dimethylacetamide was substituted for the benzamide and a solution of 11.6 g aniline in 50 ml of benzene was utilized. Workup as in Example 1 yielded N,N-dimethyl-N-phenylacetamidine in form of a colorless oil, b.p. 73° C. at 0.12 mm of mercury in only 53% yield based on aniline or 49% yield based on POCl₃ and a meager 19.5% yield based on the acetamide.

EXAMPLE 4

The procedure of Example 3 was repeated except that to the reaction mixture of equimolar reactants (0.375 mole, each), 34.9 g of aniline was added as a solution in N,N-dimethyl-N-phenylacetamidine (60 ml). Waterwash, stripping of the solvent and vacuum distillation yielded 58.8 g of the amidine, in addition to that used as a solvent, thus giving a 96.7% yield of the newly formed N,N-dimethyl-N'-phenylacetamidine product.

EXAMPLE 5

N'-Cyclohexyl-N,N-dimethylbenzamidine

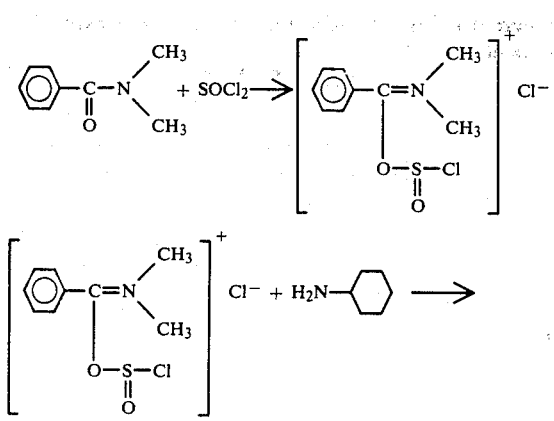

—continued

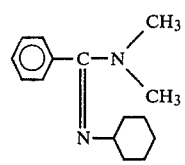

The conventional procedure of Example 1 was repeated except that 30 g (0.25 mole) of thionyl chloride was added to the chilled mixture of the benzamide in toluene (100 ml). After the addition was completed, the reaction mixture was stirred at between 5°–10° C., then a solution of 50 g (0.5 mole) of cyclohexylamine in 50 ml of toluene was added, dropwise, keeping the temperature below 30° C. by outside cooling. Waterwash, followed by caustic wash yielded an upper toluene layer which, after stripping under aspirator vacuum, yielded the amidine b.p. 78°–79° C., $n_D$ 21.6, 1.5400, in 56.0 g or 89% yield.

EXAMPLE 6

1-Methyl-2-(butylimino)pyrrolidine

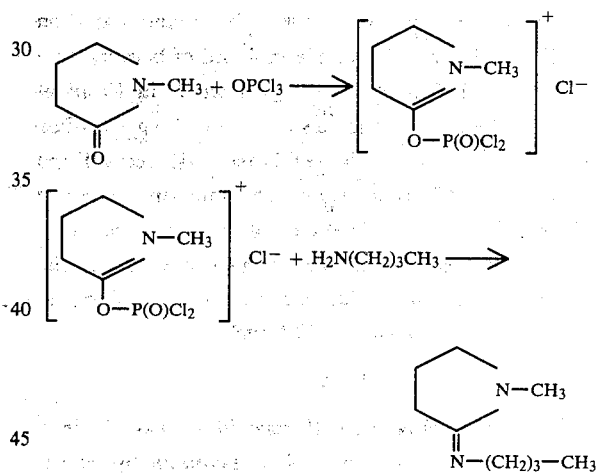

This example illustrates another embodiment of the process of the invention.

To a solution of 24.8 g (0.25 mole) of 1-methyl-2-pyrrolidine in 100 ml of methylene chloride was added, dropwise, 38.3 g (0.25 mole) of POCl₃. After the exothermic reaction subsided, 0.25 mole of n-butylamine was slowly added, followed by 50 g of a 50% aqueous sodium hydroxide solution. Waterwash, stripping of the solvent were followed by distillation of the amidine, b.p. at 30°–31° C. at 0.11 mm, $n_D$ 22.5, 1.4710, which was obtained 33.6 g or 87% yield of the theory.

EXAMPLE 7

N,N-Dimethyl-N'-phenylformamidine

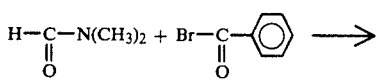

-continued

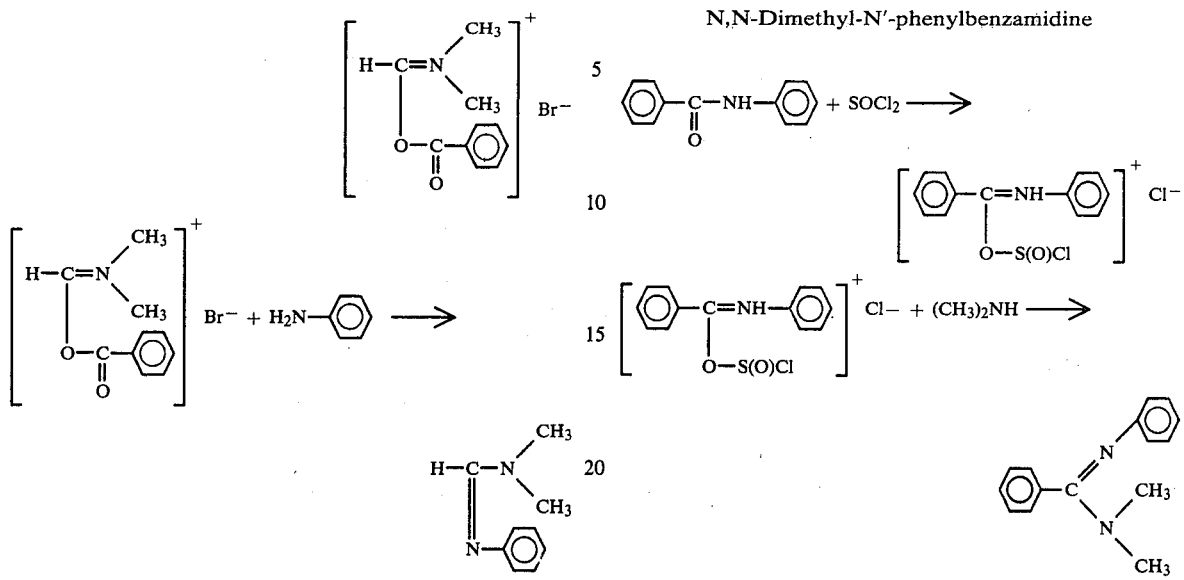

This example follows the conventional methods disclosed in the above-identified references.

To a reaction mixture, obtained by adding a solution of 23.1 g of benzoyl bromide in 40 ml of benzene to a solution of 18.2 g of dimethylformamide in 40 ml of benzene, there was added a solution of 11.6 g of aniline in 30 ml of benzene, the solids were filtered off and treated with 50 ml of water. The solution was made alkaline, extracted with ether and after evaporation of the solvent, the residue was distilled in vacuum. The titled amidine was obtained as an oil boiling at 130°–134° C. at 11 mm, in 32% yield.

EXAMPLE 8

N,N,-dimethyl-N'-phenylformamidine was obtained using the improved process of this invention by repeating the procedure of Example 7 with the stoichiometric proportion of benzoylbromide (46.2 g) and aniline (23.2 g). After the aniline addition was finished, 50 g of a 50% solution of aqueous sodium hydroxide was added, with cooling, to keep the temperature of the reaction mixture below 35° C. Workup as in Example 7 yielded N,N-dimethyl-N'-phenylformamidine in 76% yield.

EXAMPLE 9

N,N-Dimethyl-N'-phenylbenzamidine

Into a slurry of 19.7 g of benzanilide (m.p. 162°–164° C.) in 200 ml of methylene chloride was added a solution of 12.0 g of thionylchloride in 50 ml of methylene chloride. After the addition was completed and the reaction mixture was stirred for one hour at room temperature, gaseous dimethylamine was introduced until the solution became saturated. Workup by filtration, waterwash, removal of the solvent and distillation afforded N,N-dimethyl-N'-phenylbenzamidine in 18.6 g or 83% yield.

EXAMPLE 10

N,N-Dimethyl-N'-phenylacetamidine

This procedure of Example 4 was repeated except that after the addition of aniline, 100 ml of a 20% aqueous solution of tetraethylammonium hydroxide was added. The titled amidine was obtained in 86.2% yield.

What is claimed is:

1. The amidine

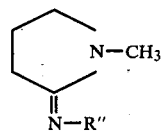

wherein R" is a $C_1$–$C_{20}$ alkyl or a $C_3$–$C_{12}$ cycloalkyl radical.

* * * * *